US007269455B2

(12) United States Patent
Pineda (10) Patent No.: US 7,269,455 B2
(45) Date of Patent: Sep. 11, 2007

(54) METHOD AND SYSTEM FOR PREDICTING AND PREVENTING SEIZURES (76) Inventor: Jaime A. Pineda, 8510 Summerdale Rd., #29, San Diego, CA (US) 92126

( * ) Notice: Subject to any disclaimer, the term of this patent is extended or adjusted under 35 U.S.C. 154(b) by 420 days.

(21) Appl. No.: 10/846,436

(22) Filed: May 14, 2004

(65) Prior Publication Data
US 2004/0267152 A1    Dec. 30, 2004

Related U.S. Application Data (63) Continuation-in-part of application No. 10/661,658, filed on Sep. 12, 2003, and a continuation-in-part of application No. 10/376,676, filed on Feb. 26, 2003, now abandoned.

(60) Provisional application No. 60/471,143, filed on May 16, 2003.

(51) Int. Cl.
*A61B 5/04* (2006.01)
(52) U.S. Cl. .................................. 600/544; 600/545
(58) Field of Classification Search ......... 600/544–545
See application file for complete search history.

(56) References Cited

U.S. PATENT DOCUMENTS

| | | | | |
|---|---|---|---|---|
| 5,743,860 A * | 4/1998 | Hively et al. | ............... | 600/544 |
| 5,857,978 A * | 1/1999 | Hively et al. | ............... | 600/544 |
| 6,304,775 B1 * | 10/2001 | Iasemidis et al. | ........... | 600/544 |
| 6,442,421 B1 * | 8/2002 | Le Van Quyen et al. | ... | 600/544 |
| 6,507,754 B2 * | 1/2003 | Le Van Quyen et al. | ... | 600/544 |
| 6,549,804 B1 * | 4/2003 | Osorio et al. | ............... | 600/544 |
| 6,597,954 B1 * | 7/2003 | Pless et al. | .................... | 607/62 |
| 6,658,287 B1 * | 12/2003 | Litt et al. | .................... | 600/544 |
| 6,678,548 B1 * | 1/2004 | Echauz et al. | ............... | 600/544 |
| 2002/0095099 A1 * | 7/2002 | Quyen et al. | ................ | 600/544 |
| 2002/0099412 A1 * | 7/2002 | Fischell et al. | ................ | 607/3 |
| 2002/0103512 A1 * | 8/2002 | Echauz et al. | ................ | 607/9 |
| 2003/0013981 A1 * | 1/2003 | Gevins et al. | ............... | 600/544 |
| 2003/0073917 A1 * | 4/2003 | Echauz et al. | ............... | 600/510 |
| 2003/0074033 A1 * | 4/2003 | Pless et al. | .................... | 607/48 |
| 2004/0039254 A1 * | 2/2004 | Stivoric et al. | ............. | 600/300 |
| 2004/0054297 A1 * | 3/2004 | Wingeier et al. | ........... | 600/544 |
| 2004/0153129 A1 * | 8/2004 | Pless et al. | .................... | 607/62 |
| 2005/0197590 A1 * | 9/2005 | Osorio et al. | ............... | 600/544 |

* cited by examiner

*Primary Examiner*—Charles A. Marmor, II
*Assistant Examiner*—Karen E Toth
(74) *Attorney, Agent, or Firm*—Procopio, Cory, Hargreaves & Savitch LLP (57) ABSTRACT A method and system for the detection and prevention of epileptic seizures utilizing bioelectric signals to assess a seizure profile (SP) and an adaptive control system for neurofeedback therapy. The inventive method and system provide the detection of changes in the non-linear dynamics of brain electrical activities to characterize and differentiate individual susceptibility to seizure onset, predict the occurrence of a seizure episode, and initiate neurofeedback training to prevent the attack.

12 Claims, 8 Drawing Sheets

METHOD AND SYSTEM FOR PREDICTING AND PREVENTING SEIZURES

CROSS REFERENCE TO RELATED APPLICATION

This application claims priority to provisional application Ser. No. 60/471,143 filed on May 16, 2003, and is a Continuation-in-Part of pending U.S. patent application Ser. No. 10/661,658, filed Sep. 12, 2003, which in turn is a Continuation-in-Part of U.S. patent application Ser. No. 10/376,676, filed Feb. 26, 2003 now abandoned, all of which applications are incorporated herein by reference in its entirety.

FIELD OF THE INVENTION

The present invention relates to the measurement of brain waives. In particular, this invention relates to a method and system for the monitoring of brain electrical activities for predicting and preventing seizures.

BACKGROUND OF THE INVENTION

For medical monitoring purposes, it is desirable to anticipate how individuals will respond to different events, whether externally- or internally-mediated, in order to maximize the effectiveness of controlling, alleviating, or preventing injurious or responses. Electroencephalogram (EEG) correlates of seizure are typically characterized by the sudden appearance of highly synchronized seizure discharges amidst background, desynchronized activity. This can occur at least several seconds before any clinical evidence of a seizure.

There are many ways to monitor an individual's condition of a possible seizure, including analysis of eye movement, EEG, EKG, and other autonomic responses. Current technology reflects technology developed 20-30 years ago in which specific EEG frequencies, for example alpha and beta waves, are analyzed to reflect general behavioral states, such as arousal or attentiveness. Characterization of these discharges is typically done visually by a professional or via traditional frequency-based signal analysis.

While these signals do correlate somewhat with an individual's attentiveness and motivational arousal, assessment and prediction of neurological disorders is yet to mature. It has been recognized that traditional analyses of EEG signals, including spectral analysis, have failed to reliably detect specific changes the precede seizures. Though current technology provides for the possibility for capturing an individual's sensory, motor, and cognitive responses to events, it does not allow for simultaneous computation or combinations of these responses. Also, it does not support the recognition of the finctional significance of the various relevant components of the signals measured in the form of bioelectric patterns. In addition, current technology does not enable real time analysis of the EEG to enable a more probing analysis of an individual's response to a stimulus event. Furthermore, though current technology tends to focus on the ongoing EEG, it does not utilize the EEG signal responses to specific events as a means to precisely assess the responses of a subject.

Accordingly, it would also be desirable to have a method and a system that enable the monitoring and characterization of an individual's (patient's) condition of a possible seizure. Also, it would be desirable to have a method and a system that incorporate real time linear and non-linear brain wave dynamics as part of an assessment protocol to enable remedial preventative therapy. Additionally, it would be desirable to provide a predictive means of the oncoming seizure attack, and to initiate remedial neurofeedback therapy to prevent or minimize the occurrence of the seizure. The present invention addresses these fundamental attributes.

SUMMARY OF THE INVENTION

The present invention comprises a method and a system for acquiring the bioelectric signals of a user, which are converted into a digital stream, processed and combined to define a cognitive-emotive profile or "state of mind" of the user. Incorporating microprocessor-based software and database capabilities, the present invention uses this cognitive-emotive profile to assess the likelihood of an impending seizure attack. The inventive system then triggers an alarm and/or initiates neurofeedback or drug therapy to prevent the occurrence of the seizure.

The present invention provides a novel, robust, and reliable assessment of the changes in an individual's (patient's) responsiveness to stimuli, regardless of whether it is visual or audio, internally- or externally-mediated that arises from the individual or combined assessment of multiple bioelectric signals. In addition to the traditional bioelectric measures of responsiveness, the present invention provides an index of the "complexity" of brain electrical activities based on the analysis of non-linearity in the EEG signal. The outcome of both linear stochastic and non-linear analyses is then combined with Independent Component Analysis (ICA) for the reduction or elimination of random noise, detection of the onset of seizure and, with neural network capabilities, enhancement of pattern recognition. The system can also compute an index of the likelihood that a seizure will occur—a seizure profile (SP), which can be recorded and displayed on a small laptop computer, a personal assistance devices (PPA) or an electronic monitoring device.

In addition to providing an SP and an alarm signal warning of its impending onset, the present invention is capable of mapping bioelectric signals into microprocessor commands in real time. It allows closed-loop feedback for remedial prevention of the seizure, thus defining an adaptive control system. The bioelectric signals captured by this system include spontaneous EEG rhythms, particularly those measured over the sensorimotor cortex, time-locked responses to external events, or event-related potentials (ERPs), steady state visual evoked responses, as well as autonomic measures of bodily states, for example, heart rate (HR) galvanic skin response (GSR) and electrooculogram (EOG).

DETAILED DESCRIPTION OF THE INVENTION

The present invention provides a method and a system, which utilizes bioelectric signals to assess a seizure profile (SP) of an individual user and to enable adaptive neurofeedback therapy to reduce and/or prevent seizure. The invention comprises means for acquiring the bioelectric signals, such as brain waves, of an individual, which are converted into a digital stream and mathematically processed to define a representation of the cognitive state of mind. Incorporating microprocessor-based software and database capabilities, the system uses this cognitive state of mind, in combination with Independent Component Analysis, (ICA) and Neural Network (NN) capabilities, to dynamically determine the likelihood of an impending seizure and graphically represents the results for easy interpretation. From such results, the system initiates a remedial preventative neurofeedback training exercise to the user to prevent the onset of the seizure. With reference to FIGS. 1-8, the invention is now described in detail.

Schematically, there are eight major components or stages involved in the present invention: 1) recording bioelectric activities; 2) real-time data analog-to-digital conversion; 3) preprocessing and analysis of the data with ICA; 4) Neural network pattern recognition; 5) computing brain complexity dynamics and defining the cognitive state of mind; 6) computing a seizure profile; 7) graphical display, and 8) closed-loop neurofeedback training.

Stage 1. Recording Bioelectric Activity

The present invention, which can be considered as an adaptive control system, incorporates the use of bio-electrical signal sensors or biosensors for the acquisition of bioelectric activities (for example, brain waves). Such sensors are commonly available, and they require a minimum of preparation or electrolytic conducting substance. The sensors are placed in proximity as needed on the scalp, forehead, or other locations of the user's or patient's body. The biosensors may be embedded in commercially available conventional electrode caps, headbands, nets, virtual reality (VR) helmets, or other means placed on the head of the user.

Figure 1:
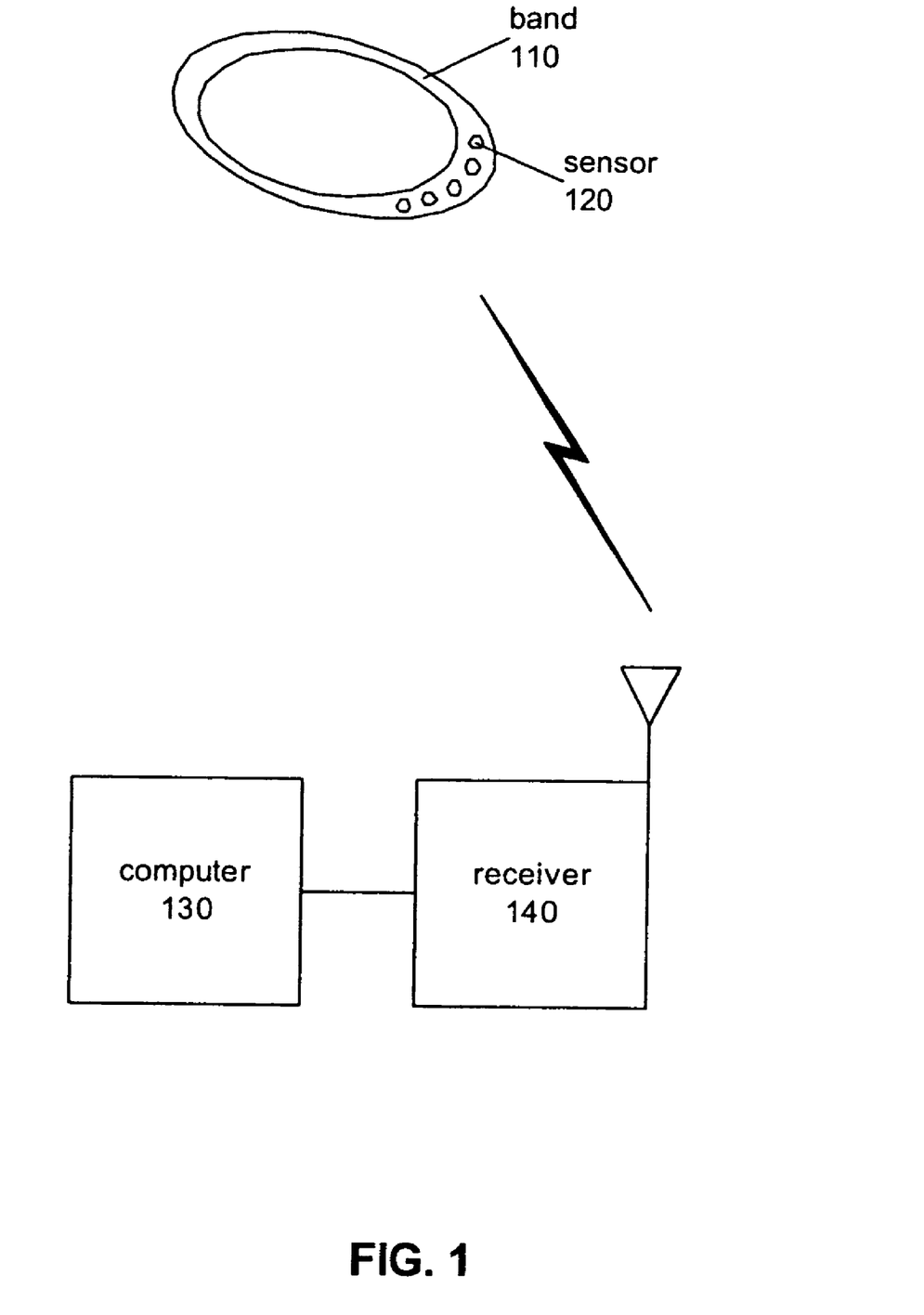
FIG. 1 schematically depicts the process and system for recording, transmitting and analyzing bioelectrical activities signals for defining a seizure profile (SP) and initiating a neurofeedback therapy protocol according to the present invention.

In the present invention, the system includes a high precision, low interference headband, which is easy to put on and operated. As illustrated in FIG. 1, a user is provided with a biosensor headband 110, which is placed on the forehead of the user (not shown). The headband 110 utilizes either disposable gel-filled inserts, saline-based electrodes, or active dry electrodes with the amplifiers built into the headset. This ensures excellent signal-to-noise and relatively noise- and artifact-free signals.

Figure 2:
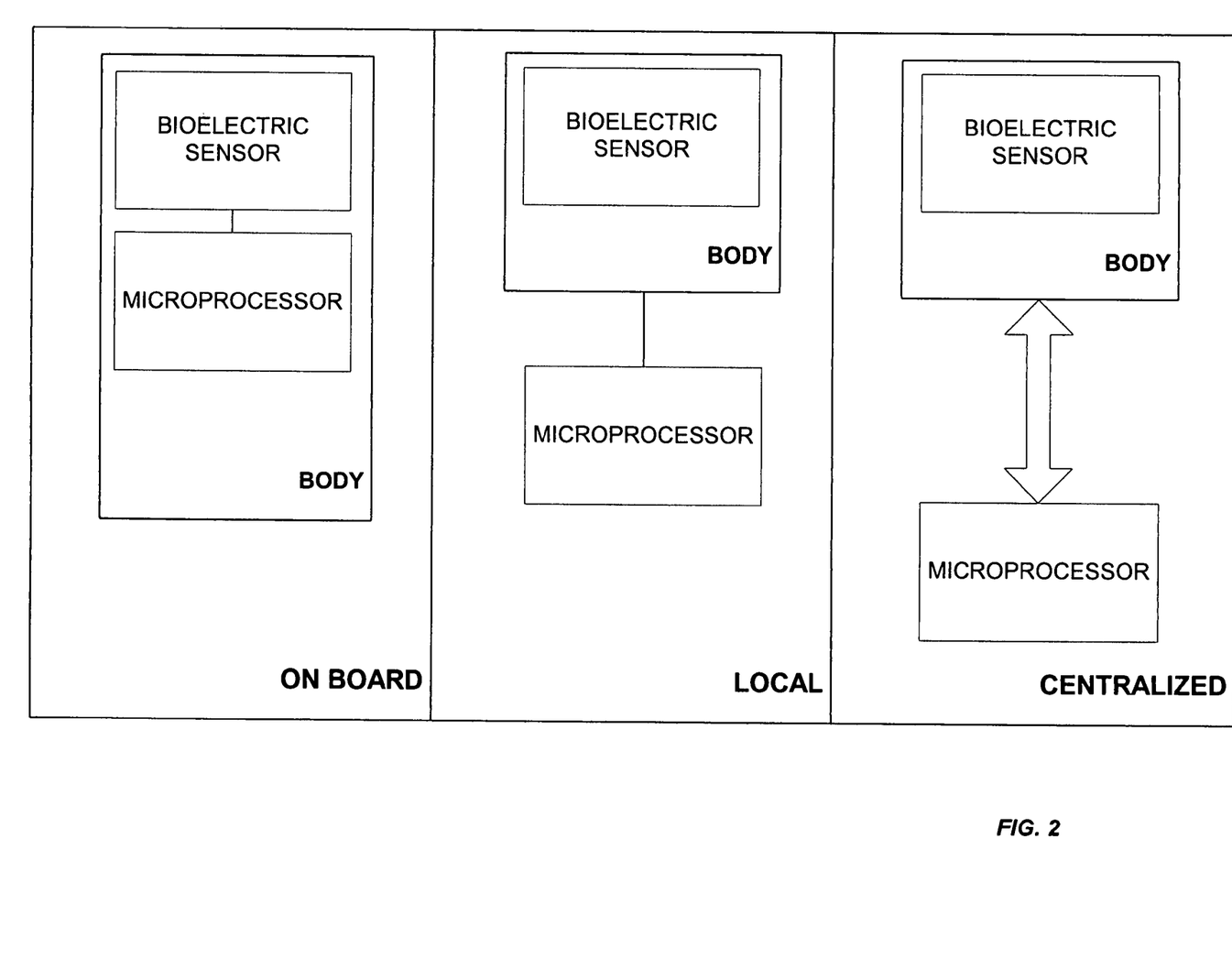
FIG. 2 depicts several alternative approaches in communicating bioelectrical activities between bioelectrical sensors and a microprocessor-based computer used for data analysis and feedback.

As illustrated in FIG. 2, the sensors-to-microprocessor link can be onboard (i.e., both sensors and microprocessor are on the body), local (both sensors and microprocessor within a defined distance of each other); or centralized (both sensors and microprocessor at a very large distance from each other).

As shown in FIG. 1, the brain signals are transmitted by wire or wireless means to a remote receiver that is connected to a microprocessor-based computing means such as a portable computer or personal device assistant type device ("PDA"). The sensors can incorporate the use either radio frequency (RF) or infrared data association (IrDA) means with built-in Object Exchange Protocol (IrOBEX) or other similar protocols. These features allow an individual to be untethered to the microprocessor or other device performing the data analysis and processing, for example, SP computations. These features thus add substantial mobility to the individual, when used in conjunction with a wireless signal transmitter, and the level of noise that typically interferes with such natural body movements can be significantly reduced.

The signal transmitting means can be incorporated as part of the headband 110. Alternatively, dedicated analog-to digital (A/D) converters can be built into the headband to digitize the analog brain signals of interests before they are transmitted by wire or wireless means to the computer.

Figure 3:
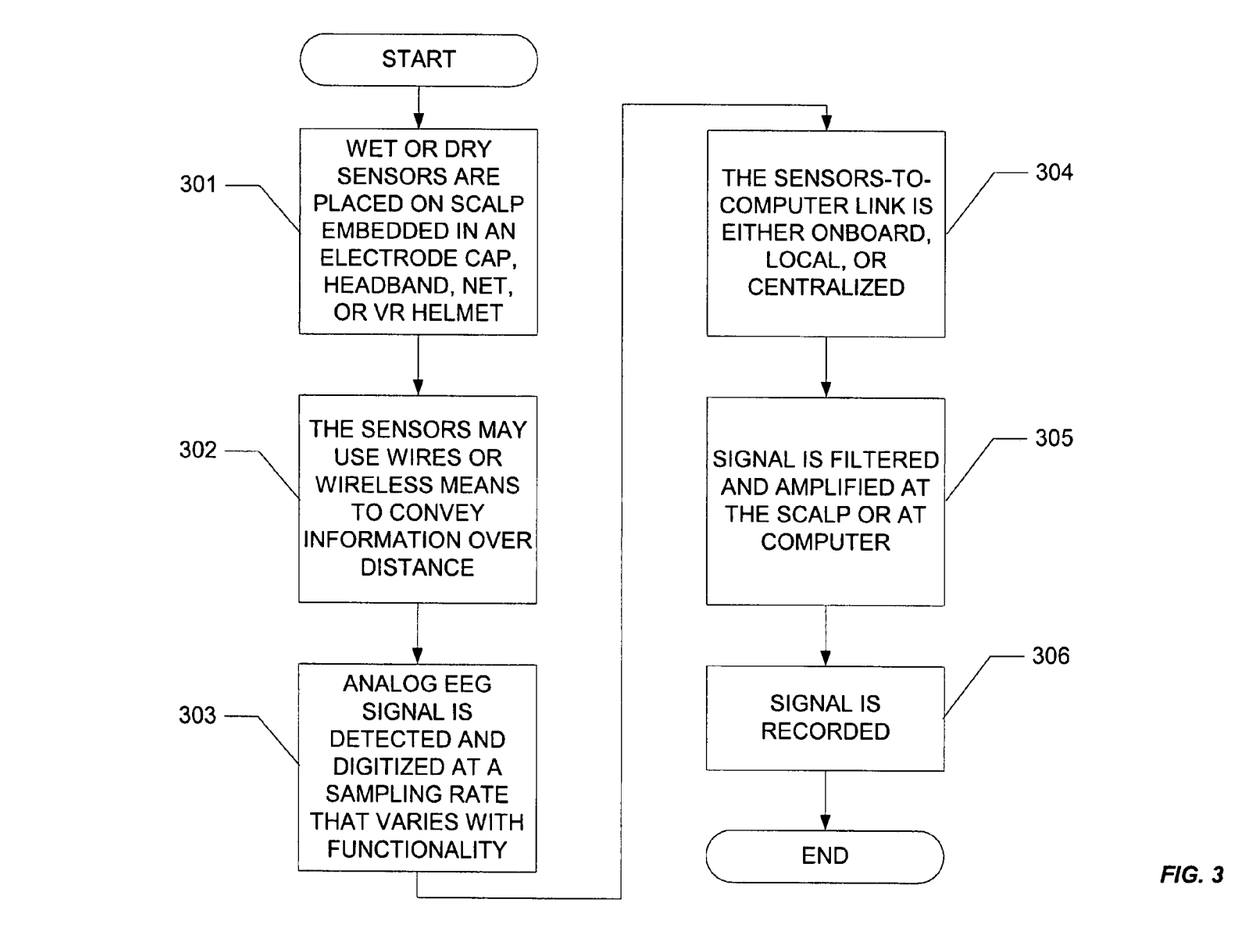
FIG. 3 is a flow chart, which shows the process of recording of brain signals.

As shown in FIG. 3, the bioelectric signals detected by the sensors on the headband 110 are digitized by an analog to digital board at a sampling rate that varies with the particular fictional requirements of the data. As an example, the use of spontaneous EEG rhythms generally requires fast sampling rates, while the use of event-related potentials would require slower sampling rates.

For purposes of illustration, three types of brain signals are acquired and analyzed in the present invention, which would be applied for computing a "sense awareness" and a "mental state awareness" indices. These signals include spontaneous EEG rhythms, time-locked responses to external events, and steady state visual evoked responses. Additionally, peripheral signals such as heart rate (HR), galvanic skin response (GSR), and electrooculogram (EOG) can also be recorded and analyzed to compute a "context awareness" index. "Context-awareness" capabilities can be activated while users are engaged in performing an instrumented and well-characterized procedure or application from which task-relevant parameters can be captured. Analysis of these data may include examination of reaction times and appropriateness of an individual's responses. For example, specific autonomic responses, such as HR, GSR, or temperature can be captured simultaneously, which can be used to assess the context awareness on the part of the individual or patient.

Stage 2. Real-Time Analog-to-Digital Conversion

The analog bioelectric signals are filtered (band passed) and amplified (either at the scalp or remotely at the recording microprocessor), and digitized in real-time. The present invention provides for the real-time analog-to-digital conversion and analysis of bioelectric signals and incorporates the use of a dedicated microprocessor-based scientific software system, which resides in the microprocessor-based computer 130 (FIG. 1). Computer 130 also includes a software system with a library of data analysis routines for processing spontaneous, event-related, and steady state brain responses and peripheral autonomic signals, including digital filtering, signal averaging, real-time power spectrum analysis, calculation of the ongoing power in different frequency bands, correlation dimension and other nonlinear analyses. The computational output is then used to provide feedback information to the user or to adapt the data analysis/extraction algorithm to best match the incoming data (adaptive data extraction).

The present invention provides two types of outputs for resource control—digital (e.g., on/off control of a device or sending digital information to a networked associate) or analog (graded), via digital-to-analog (D/A) converters. A feature of the invented system is its ability to analyze incoming data in real-time, as it is acquired, which then triggers a command based on the result of the analysis.

The present invention uses a simple uniform structure for data representation with the same data format for both input and output data (the raw incoming data and the results of an analysis) to ensure, among other things, that the output of one program can be used as an input for another. Data already collected and pre-processed can be reused and analyzed in a different way. The invention also supports the export of data in a format that can be used by other microprocessor-based software programs to perform independent component analysis or neural network analysis.

Stage 3. Preprocessing and Analysis of the Data With ICA (Signal Decomposition)

Figure 4:
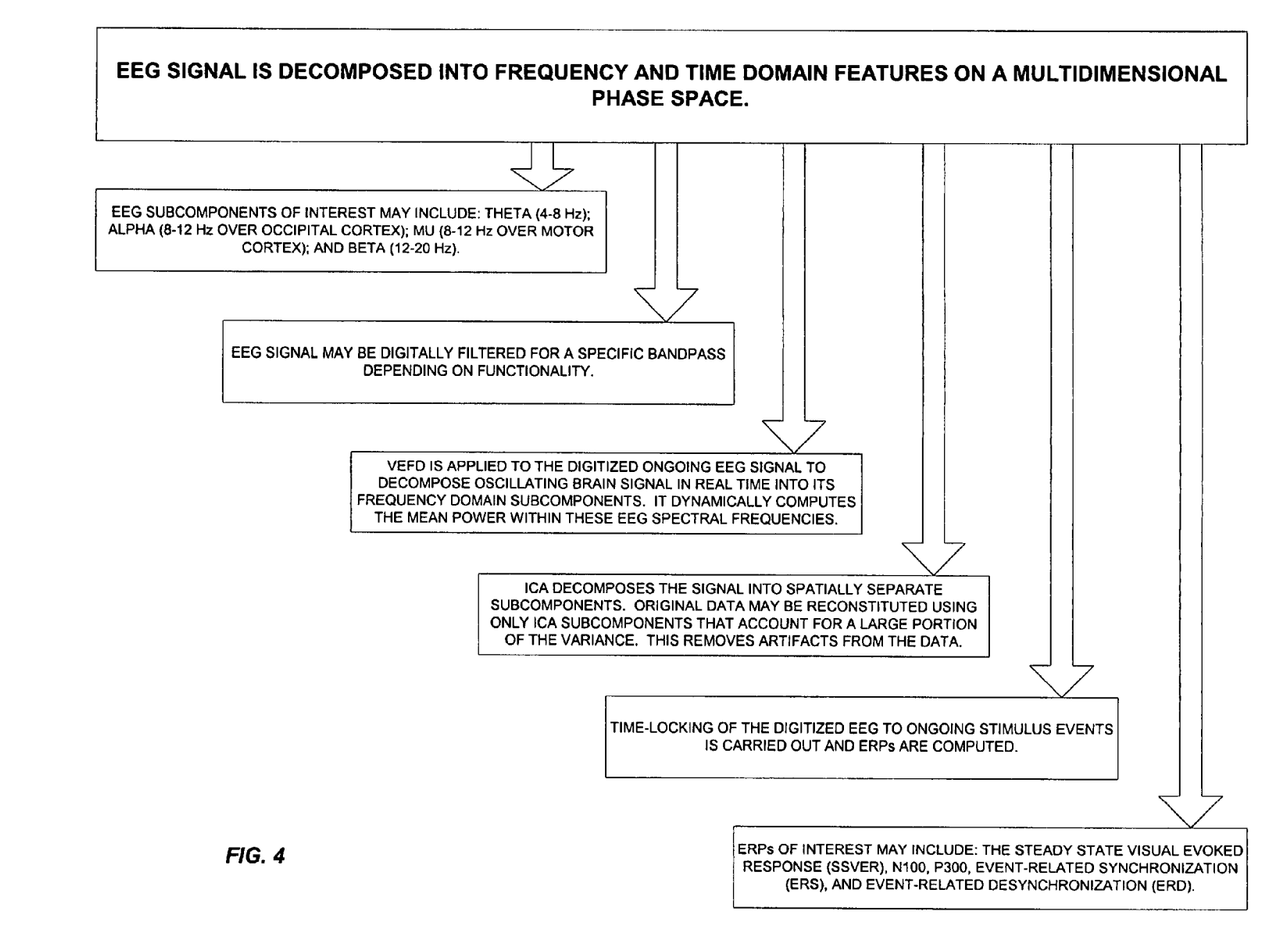
FIG. 4 is a flow chart, which shows the decomposition and analysis of bioelectrical activities (brain signals)

As shown diagrammatically in FIG. 4, the digitized EEG signal recorded from the brain of the individual or patient is decomposed into frequency and time domain features on a multidimensional phase space. The frequency and time domain subcomponents are analyzed using a variety of techniques including Independent Component Analysis (ICA), Variable Epoch Frequency Decomposition (VEFD), Fast Fourier Transform, Event-Related Potentials (ERPs), Time-Frequency Expansion, and/or Feature Coherence Analysis, among others. The EEG subcomponents of interest include EEG rhythms, such as mu (7-13 Hz over sensorimotor cortex), theta (4-8 Hz); alpha (8-12 Hz over occipital cortex); and beta (12-20 Hz). They also include time-locked responses to external events, or event-related potentials, such as the traditional N1,P3,or the steady state visual evoked response (SSVER) and peripheral autonomic signals (e.g., HR, GSR, and EOG). The signals are digitally filtered for a specific band pass depending on which of these signals is (are) being used.

In some applications of the present invention, VEFD, which is a unique algorithm to quickly and efficiently analyze bioelectric signals in real time, is applied to the digitized ongoing signal to decompose oscillating rhythms into their frequency domain subcomponents. For example, in order to determine how tired a user is, the system examines the level of alpha and beta activities in the EEG. In the present invention, VEFD can provide for a robust method of brain signal detection.

In other applications, ICA is applied to decompose the signal into spatially separable subcomponents, which maximizes the signal-to-noise response and allows for multiple control signals. Such application enables the reconstitution of original data with only ICA subcomponents that account for a large portion of the variance in the signal. This removes blinks, eye movements, and other artifacts from the data. Using ICA to "clean" the data in real time increases the signal-to-noise ratio and make the relevant signal easier and faster to detect by a pattern recognition system. The use of ICA thus provides a solution to the problem of blind source separation, which is analogous to the one posed by recording bioelectric signals at multiple sites where the signal at any recording site (be it a satellite, microphone, or electrode) is assumed to consist of a combination of numerous overlapping sources. The locations of these sources are unknown, and the objective is to isolate the contribution of each of these independent sources based on the observed data at each site. Identification of multiple independent control signals in the input makes simultaneous control of multiple functions feasible in the present invention, for example, as in signaling a patient, health care provider, or a central site, and in initiating the neurofeedback therapy protocol.

Stage 4. Neural Network Pattern Recognition

Figure 5:
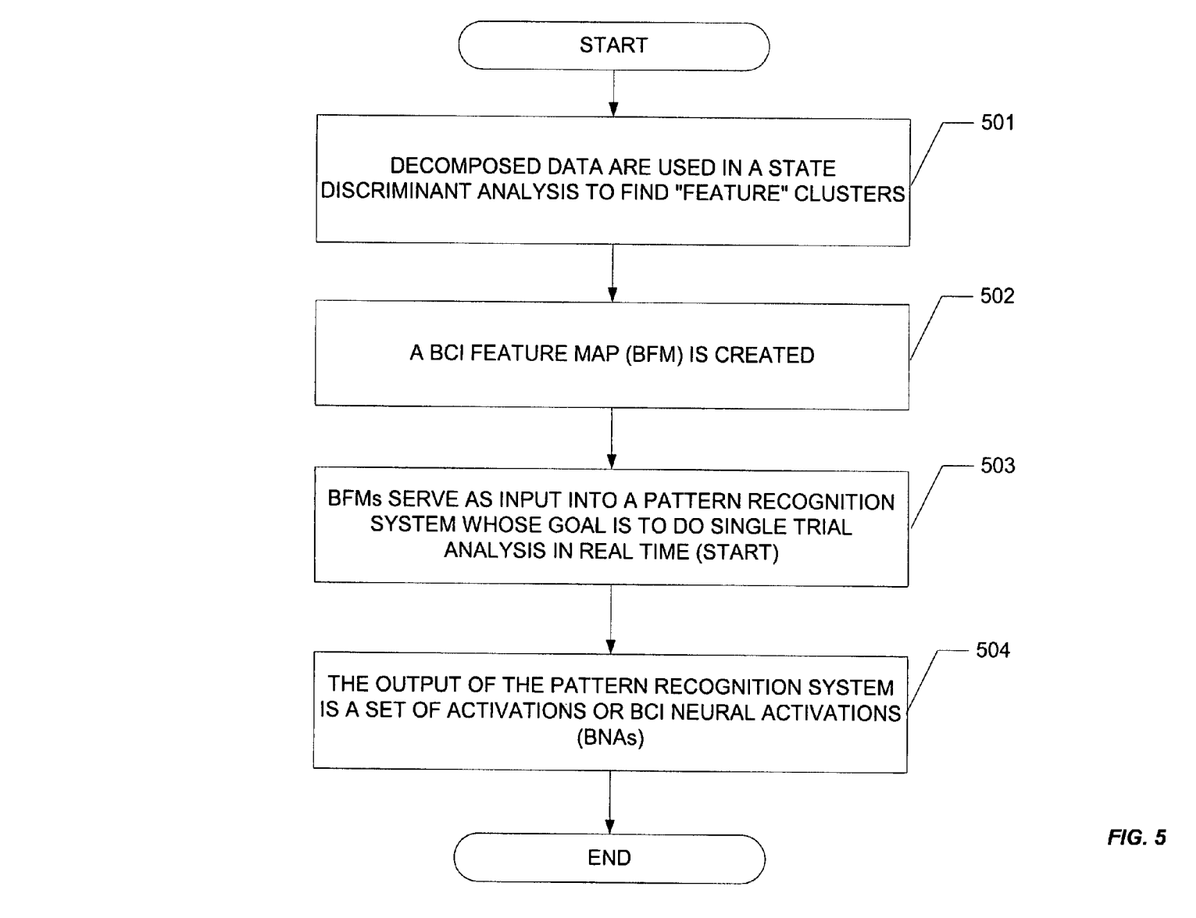
FIG. 5 is a flow chart, which shows the learning and pattern recognition analysis of brain signals.

FIG. 5 illustrates the steps in stage 4 whereby decomposed EEG data in the computer are resolved by way of a state discriminant analysis to identify "feature" clusters that are most reliably different between various conditions (Step 501). These feature clusters represent patterns of electrical activities or signal dynamics that occur across the scalp, which are considered linked to specific motor or non-motor thought patterns. For example, when a user sees a novel image on the screen, a large positive-going voltage can be detected over the middle of the scalp approximately 300 milliseconds after the onset of the novel image. This would be a feature cluster easily identified in this type of discriminant analysis. This may be accomplished using: waveform analysis, distribution function analysis, Fuzzy logic, and/or discriminant optimization, among others analytical techniques. The outcome of this analysis is the definition of a BCI Feature Map (BFM), which is represented as a set of parameters, components, functions, and criteria (Step 302).

A plurality of the BFMs are constituted as inputs into a pattern recognition system, which may be expressed in the form of a probabilistic neural network (Step 505). Other types of pattern recognition systems that may be used in addition to a neural network includes genetic algorithms, Kohonen networks, Fuzzy neural nets, and Markov models. The output of the pattern recognition system is a set of activations or BCI Neural Activations (BNAs) (Step 504), which defines the cognitive state of mind of the individual subject or patient before, during and after a seizure or epilepsy episode, which is an essential part of the Seizure Profile, as described in more detail below. In the present invention, the BNAs are derived from the adaptive combinations of discriminant brainwave features in space, time, frequency, and phase that come together to maximize the contrast between the various parameters.

The patterns of brain activities in the present invention are classified in real time. Neural networks, or other pattern recognition systems or techniques, are used to determine the underlying functional relationship between power spectrum fluctuations or the changes of linear stochastic and nonlinear characteristics of the EEG associated pre-seizure states. Employing a neural network classifier with modifiable parameters enables the following: (a) underlying relationships which are assumed to exist, are not known, and are to be found; (b) by supplying the neural network with training sets obtained from recordings on single individual, patient, or subject, the network "learns" individual patterns; and (c) the method can be adjusted to correspond to the results obtained by visual inspection of different experts. This approach enables the recognition of complex patterns such as the ones produced by sensor arrays as in the present invention for the categorization of bioelectric patterns. It also enables rapid and reliable recognition and learning of brain patterns that are consistently mapped to the pre-seizure states as customized for the particular subject or patient.

Stage 5. Computing Brain Complexity and a Cognitive State of Mind

As commonly recognized, the EEG correlates of a seizure episode are typically characterized by the sudden appearance of highly synchronized seizure discharges amidst background, desynchronized activities, which represent highly irregular behaviors of complex systems. This can occur as little as several seconds before any clinical evidence of the seizure, and characterization of these discharges is typically done visually by a health care professional or via traditional frequency-based signal analysis. However, such traditional analysis is quite unreliable in identifying certain bioelectrical activities in the patient. To overcome the failure of traditional analyses of EEG signals, including spectral analysis, and to reliably detect specific changes that precede the onset of seizures, the present invention incorporates the use of nonlinear dynamics analyses for the evaluation of the bioelectrical signals that are marked by changes of temporal transitions from high- to low-dimensional system states. These analyses have indicated that the evolution toward a seizure involves a pre-seizure transitional phase of several minutes that is not detected by linear techniques.

In the present invention, the non-linear dynamics algorithm for analyzing the brain complexity is based on a non-linear method used for analyzing time series in the form of a correlation dimension analysis, which yields a correlation dimension:

$$C(R) = \lim_{N \to \infty} \frac{1}{N^2} \sum_{i=1}^{N} \sum_{j=1}^{N} \Theta(R - |\vec{x}_i - \vec{x}_j|), (i \neq j)$$

Where R is a certain distance, $\vec{x}$ are vectors of the state space and $\Theta$ the Heavyside function. C(R) denotes the probability that two arbitrary points of the state space will be separated by a distance smaller than R and behaves as a power of $C(R) \sim R^{Dx}$. The dimensionality can be computed by plotting logC(R) versus logR. The output of this correlation analysis becomes the input into the neural network, and it forms the basis for the Seizure Profile, as detailed below.

Stage 6. Computing a Seizure Profile

The application of the correlation dimension analysis on the bioelectric data (raw EEG) produces a set of values that is associated with a patient's cognitive state of mind. This is first applied to a patient's period of normal or non-seizure (non-epilepsy) related EEG, and the values are defined as a reference EEG window. The reference EEG window is then compared with a similar scanning EEG window (also with correlation dimension analysis) of the patient's EEG that is moved forward in time towards known seizure onsets. The moving window allows for a determination of a "dynamical similarity index (DSI)," which represents the extent to which the reference EEG and the scanning window are similar and defines a Seizure Profile, which is a graphical representation of the DSI. When statistical differences between the reference and scanning windows reach a threshold, a pre-seizure state is declared.

As discussed above, the present invention employs Probabilistic Neural Networks (PNNs) functions to complement pattern recognition and other robust classifiers with their abilities to generalize, in making decisions about imprecise input data. In the present invention, PNNs receive as input the DSIs computed from various sensor channels, autonomic responses such as HR, GSR, and EOG, as well as other bioelectric signals, and learn to associate these indices with the occurrence of pre-seizure states. In addition, PNNs may also be applied to the present invention, where the input variables are measurements used to drive an output actuator, while the network also learns the control function.

Figure 7:
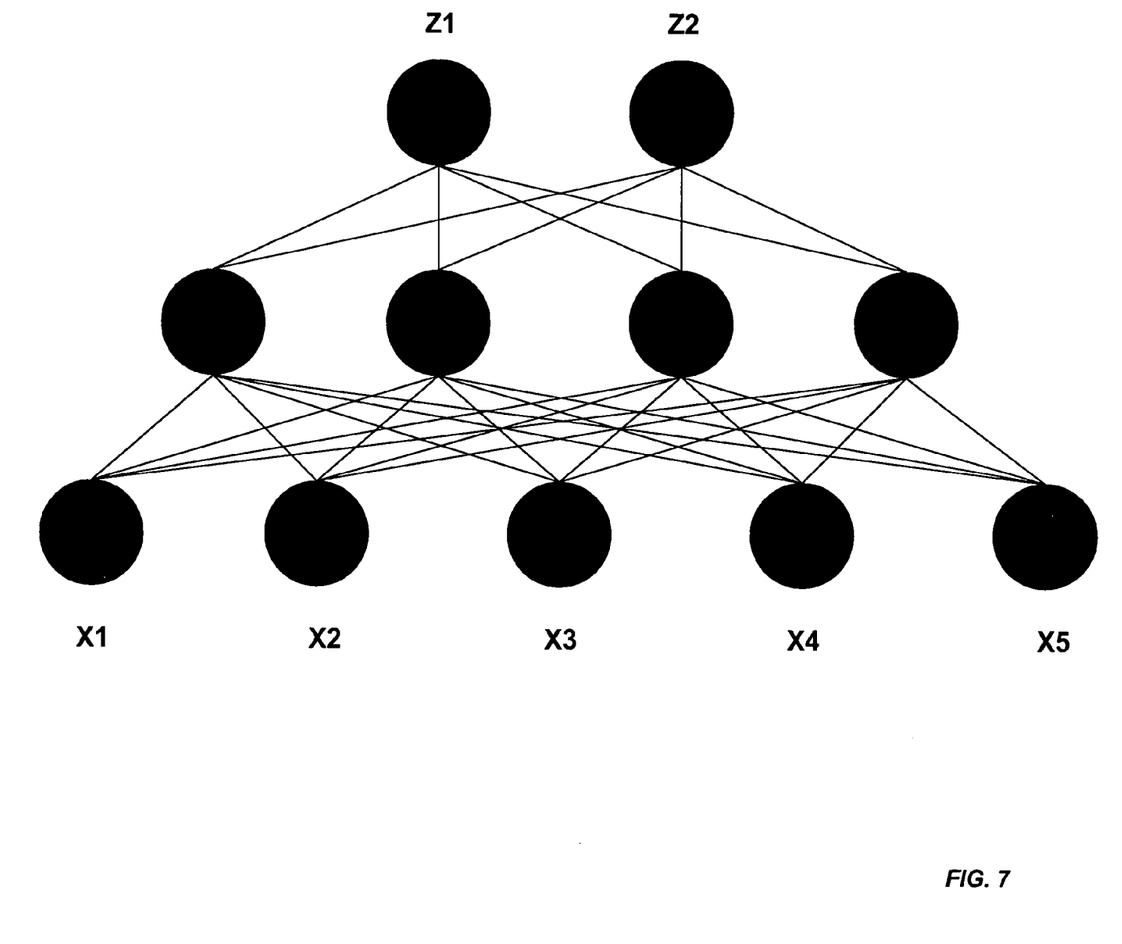
FIG. 7 shows an exemplary neural network which can be used by the present invention.

As an example, the structure of a neural network is represented in FIG. 7 where the bottom layer represents the input layer, in this case with 5 inputs labeled X1 through X5. These inputs comprise various bioelectric indices, such as the DSIs, which can be extracted from different recording sites simultaneously. In the middle of the network is the hidden layer, with a variable number of nodes. It is the hidden layer that performs much of the work of the network. Each node in the hidden layer is fully connected to the inputs. The hidden layer is where the network learns interdependencies in the model. FIG. 7 illustrates predefined relationship for the manipulation and translation of the brain signal into the output functions associated with the output layer, which comprises at least one node.

Figure 8:
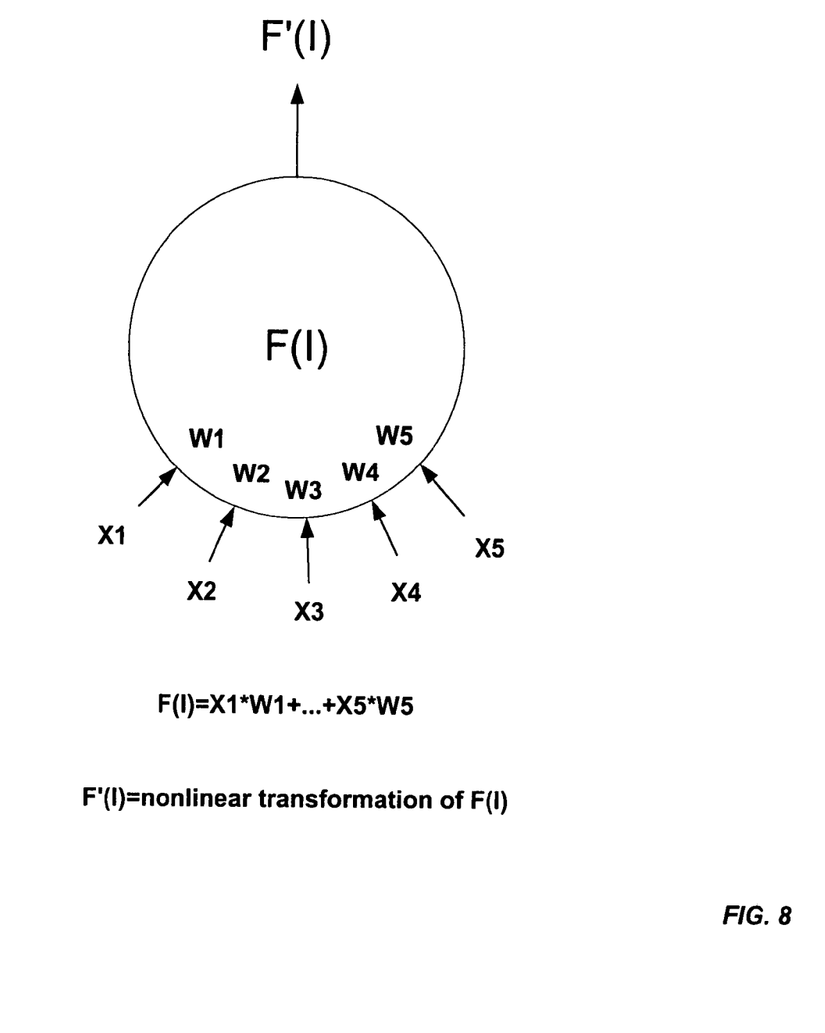
FIG. 8 shows an exemplary computational algorithm for manipulating input signals.

The computation to determine the interdependencies among various bioelectric events involves a two-layer feedforward neural network that involves a weighted sum: X1 times W1 plus X2 times W2 on through X5 and W5, as illustrated in FIG. 8. It consists of two layers of weights (the neural network name for the model parameters) and two (or three) layers of "neurons'" (or units). The first layer of neurons is not usually counted as a layer: It is the input to the neural network. The second layer is the hidden layer. The neurons in this layer have an activation function, and it is necessary for the non-linearity of neural network that this activation function is non-linear. The final layer is the output layer. These will also have an activation function. This might be linear or non-linear.

With "x" as the input, "y" as the output (Seizure Profile), with "v" as the first layer of weights (the input-to-hidden weights) and "w" as the second (the hidden-to-output weights) and with i, h, o, and p as the indices for the input, hidden and output neurons, and the examples, respectively, the following neural network function is obtained:

$$y_o^p = g^o\left(\sum_{h}^{n_b} w_{ho} g^h\left(\sum_{i}^{n_j} v_i h x_i^p + v_{h0}\right) + w_{o0}\right)$$

Here, $g^o$ and $g^h$ are the activation functions and $V_{h0}$ and $w_{o0}$ are the biases.

During training, the network is repeatedly presented with observations from available data related to the problem to be solved, including both inputs (the X1 through X5 in the diagram above) and the desired outputs (Z1 and Z2 in the diagram). The network predicts the correct output for each set of inputs by gradually reducing the error (backpropagation of error algorithm). In addition to the use of neural networks, other algorithms, such as learning vector quantization, radial basis function, Hopfield, and Kohonen, can also be used to assess the interdependencies of the various brain activities.

Stage 7. Graphical Display and Closed-Loop Neurofeedback Training

Figure 6:
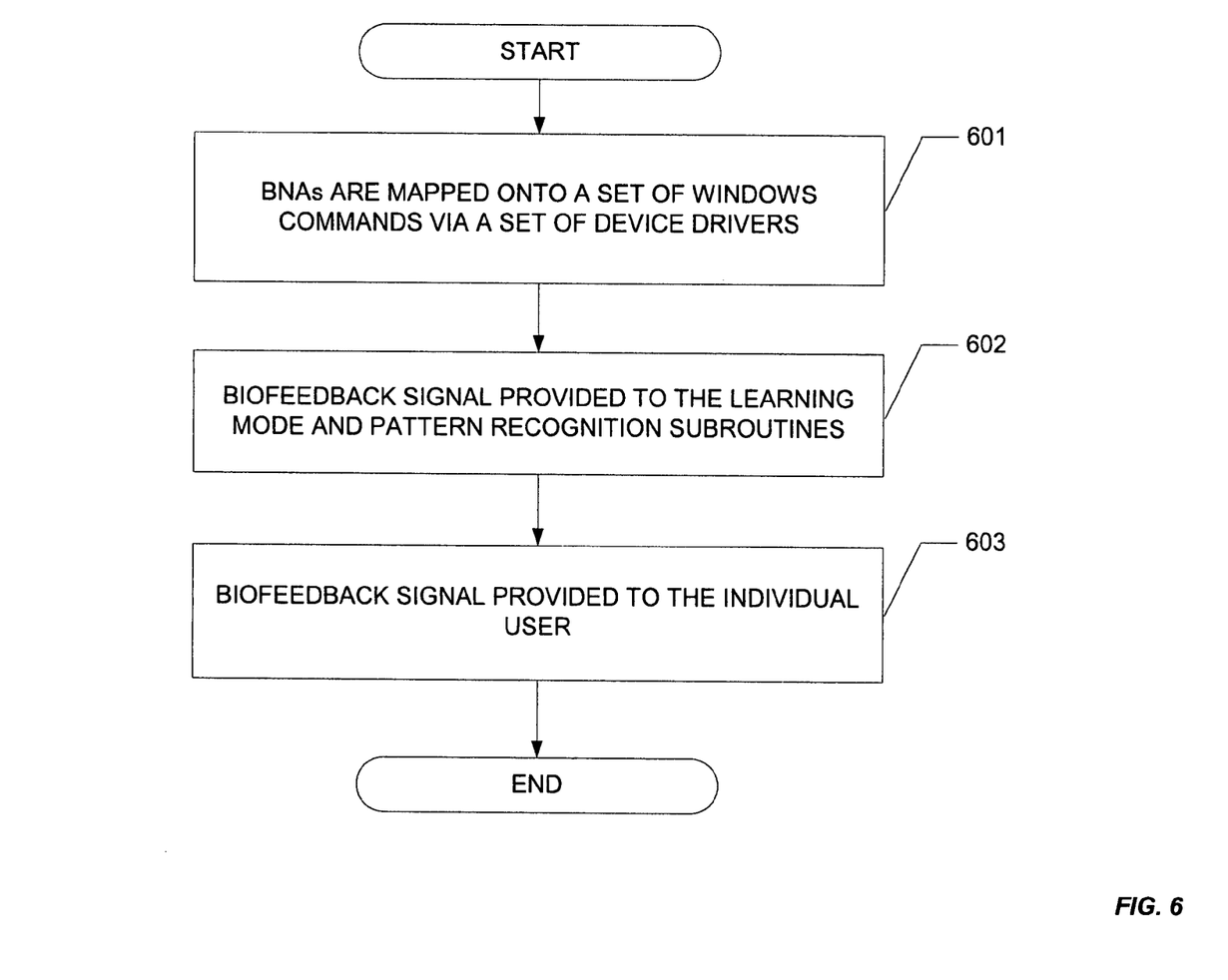
FIG. 6 is a flow chart diagram, which shows a computer interface and closed-loop feedback analysis of brain signals.

The SP is both a dynamic computation of changes in the EEG from a normal baseline and the historical trend of those changes as it nears pre-seizure and seizure states. They can be graphically displayed in this invention as a visual representation of the likelihood of a seizure episode. In addition, once a pattern of brain activity is identified (in this case a predicted seizure), the BNAs can activate an audible or visual alert. Further, the BNAs can be dynamically mapped onto a set of microprocessor-based system commands, (Step 601) as depicted in FIG. 6. By way of examples, the commands may include Windows® commands for keyboard command, cursor movement control, file operation, and protocol control. When an seizure attack is imminent, the alarm can be triggered to initiate a set of neurofeedback exercises to prevent the attack from occurring (Step 602). More specifically, a neurofeedback protocol or biofeedback exercise is initiated whereby the user attempts to gain control of brain rhythms that may show signs of disturbance during pre-seizure states. Such neurofeedback (Step 603) also reduces levels of stress, calms the individual down, and regulates brain activity to prevent the onset of the seizure. The feedback could also be adapted as a control mechanism for the automatic delivery of anti-epileptic drug therapy or vagal nerve stimulation to arrest the oncoming seizure.

The dynamic mapping also allows advantages in several "open-loop" situations where the user does not necessarily need to detect and employ feedback to achieve robust assertion of a desired control. Additionally, the present invention enables the monitoring of changes in brain dynamics while individuals sleep or go about their daily chores and provides a dynamic visual display of their seizure profile.

As discussed above, the inventive method and system enables the detection of changes in the non-linear dynamics of brain electrical activities to characterize and differentiate individual susceptibility to seizure onset, predict the occurrence of a seizure episode, and initiate neurofeedback training in order to prevent the attack. Thus, the invention represents a unique, novel, more reliable, real time adaptive system for the assessment of an individual's or patient's likelihood of experiencing a seizure episode. It takes into account the linear stochastic and non-linear details of brain dynamics and reflects the user's cognitive state of mind. This is coupled with new analysis techniques to determine how likely an individual is to experience a seizure episode. In addition, this invention has many other applications, most particularly in the prediction of migraine headaches, which are thought to reflect a type of seizure and seizures associated with diabetic hypoglycemia, fibromyalgia, or chronic pain.

While the above description of the invention is directed to the present embodiments or examples of applications, various modifications and improvements can be made without departing from the spirit and scope of the invention.

I claim:

1. A method for the detection of seizures comprising the steps of:
    (i) acquiring a first bioelectric signal and a second bioelectric signal of a human subject,
    (ii) processing the first of bioelectric signals to define a baseline cognitive state of mind window for the subject,
    (iii) processing the second bioelectric signal to define a moving cognitive state of mind window for the subject, and
    (iv) comparing the baseline bioelectric signal window with the moving bioelectric signal window to define a dynamical similarity index indicative of the likelihood of a seizure.

Wherein the dynamic similarity index analysis is optionally applied to neural network analysis to define the correlation between the bioelectric signals and the occurrence of pre-seizure states and wherein the correlation between the bioelectric signals and the occurrence of pre-seizure states are supported by a Neural Networks (NN) function wherein the NN function is in the form of $$y_o^p = g^o\left(\sum_h^{n_h} w_{ho} g^h\left(\sum_i^{n_j} v_i h x_i^p + v_{ho}\right) + w_{oo}\right)$$

where "x" is the bioelectric DSI; "y" is the seizure Profile; "v" is the first layer of weights (the input-to-hidden weights); "w" is the second (the hidden-to-output weights); and I, h, o, and p are the indices for the input, hidden and output neurons.

2. The method according to claim 1 wherein the correlation between the bioelectric signals and the occurrence of pre-seizure states are supported by at least one of the algorithmic functions selected from learning vector quantization, radial basis function, Hopfield, and Kohonen.

3. The method according to claim 1 wherein the bioelectric signals comprises Electroencephalograph rhythms (EEG's).

4. The method according to claim 3 wherein the EEG's comprises at least one of mu, theta, alpha, N1, P3, SSVER signals.

5. The method according to claim 1 wherein the bioelectric signals are processed according to time and frequency domain subcomponents with at least of one the techniques selected from Independent Component Analysis, Variable Epocl Frequency Decomposition (VEFD), Fast Fourier Transformation, Event-Related Potentials, Time-Frequency Expansion, and Feature Coherence Analysis.

6. The method according to claim 1 wherein nonlinear dynamics analyses are applied in defining the dynamical similarity index.

7. The method according to claim 6 wherein non linear dynamics analyses are supported by a cross correlation integral in the form of:

$$C(R) = \lim_{N \to \infty} \frac{1}{N^2} \sum_{i=1}^{N} \sum_{j=1}^{N} \Theta(R - |\vec{x}_i - \vec{x}_j|), (i \neq j)$$

where R is a certain distance, are vectors of the state space and the Heavyside function. C(R) denotes the probability that two arbitrary points of the state space will be separated by a distance smaller than R and behaves as a power of C(R)~RDx.

8. The method according to claim 1 which further comprises the step of administering a therapeutic anti-epileptic drug or vagal nerve stimulation to the subject.

9. The method according to claim 1 which further comprises the step of mapping the seizure profile onto a set of microprocessor system commands for controlling the external environment of the subject.

10. The method according to claim 9 wherein the microprocessor system commands further activate at least one of an audio signal or a visual signal therapeutically communicated to the subject.

11. The method according to claim 1 wherein the dynamical similarity index analysis is optionally applied to neural network analysis to define the correlation between the bioelectric signals and the occurrence of pre-seizure states.

12. The method according to claim 1 wherein the correlation between the bioelectric signals and the occurrence of pre-seizure states are supported by Neural Networks (NN) function.

* * * * *